United States Patent
Natale

(10) Patent No.: US 6,764,486 B2
(45) Date of Patent: Jul. 20, 2004

(54) ABLATION DEVICE FOR CARDIAC TISSUE, ESPECIALLY FOR FORMING A CIRCULAR LESION AROUND A VESSEL ORIFICE IN THE HEART

(75) Inventor: Andrea Natale, Cleveland, OH (US)

(73) Assignee: Biotronik Mess- und Therapiegeräte GmbH & Co. Ingenieurbüro Berlin, Berlin (DE)

(*) Notice: Subject to any disclaimer, the term of this patent is extended or adjusted under 35 U.S.C. 154(b) by 0 days.

(21) Appl. No.: 10/128,576

(22) Filed: Apr. 24, 2002

(65) Prior Publication Data

US 2003/0204183 A1 Oct. 30, 2003

(51) Int. Cl.[7] .............................................. A61B 18/18
(52) U.S. Cl. ..................................................... 606/41
(58) Field of Search ................................ 606/27–52

(56) References Cited

U.S. PATENT DOCUMENTS

| 5,239,999 A | | 8/1993 | Imran | |
|---|---|---|---|---|
| 5,487,385 A | | 1/1996 | Avitall | |
| 5,738,683 A | * | 4/1998 | Osypka | 606/47 |
| 5,775,327 A | * | 7/1998 | Randolph et al. | 600/374 |
| 5,971,983 A | * | 10/1999 | Lesh | 606/41 |
| 6,071,279 A | * | 6/2000 | Whayne et al. | 606/41 |
| 6,102,908 A | * | 8/2000 | Tu et al. | 606/41 |
| 6,120,500 A | * | 9/2000 | Bednarek et al. | 606/41 |
| 6,572,612 B2 | * | 6/2003 | Stewart et al. | 606/41 |
| 2002/0022839 A1 | | 2/2002 | Stewart et al. | |

FOREIGN PATENT DOCUMENTS

| WO | WO 95/31111 A1 | 5/1995 |
|---|---|---|
| WO | WO 98/49957 A1 | 11/1998 |
| WO | WO 01/37925 A2 | 5/2001 |

OTHER PUBLICATIONS

U.S. patent application Ser. No. 2002/022839 a1, Stewart et al., filed Feb. 21, 2002.

* cited by examiner

Primary Examiner—Roy D. Gibson
Assistant Examiner—Peter J Vrettakos
(74) Attorney, Agent, or Firm—Browdy and Neimark

(57) ABSTRACT

An ablation device for cardiac tissue, especially for forming a circular lesion around a vessel orifice in the heart, comprises a steerable catheter that is provided in the region of its distal end with an abutment device for holding the distal end of the catheter on a cardiac vessel orifice; and a linear ablation applicator that is disposed distally or proximally relative to the abutment device of the catheter and can be brought from a straight passive position into a radially expanded, approximately circular-arc-type encircling ablation position.

6 Claims, 1 Drawing Sheet

ABLATION DEVICE FOR CARDIAC TISSUE, ESPECIALLY FOR FORMING A CIRCULAR LESION AROUND A VESSEL ORIFICE IN THE HEART

BACKGROUND OF THE INVENTION

1. Field of the Invention

The invention relates to an ablation device for cardiac tissue, especially for forming a circular lesion in the region of a vessel orifice in the heart, comprising a catheter that is provided in the region of its distal end with an abutment device for holding the distal end of the catheter on a cardiac vessel orifice; and a linear ablation applicator that is disposed distally or proximally relative to the abutment device of the catheter and can be brought from a straight passive position into a radially expanded, approximately circular-arc-type encircling ablation position.

2. Background Art

Regarding the background of the invention it can be stated that catheter ablation is a therapy that is used to an increasing degree to treat certain types of arrhythmia. In the process, a lesion—i.e., a denaturation of tissue along the line of a tissue ablation or tissue scarring—is created with the aid of the ablation applicator of the catheter at a certain location in the myocardial tissue in order to sever the faulty electrical stimulus pathways at that location that are responsible for the arrhythmias. The introduction of energy into the myocardial tissue via the ablation applicator, as a rule, takes place by means ablation electrodes that operate with high-frequency current. Other forms of energy, such as microwave energies, high-energy direct current or, in principle, other denaturing mechanisms, such as freezing or chemicals (e.g., alcohol), may furthermore also be used for the ablation. The term "ablation applicator", as it is used in the present application also in connection with the invention, shall always mean all of the listed ablation options, with ablation electrodes representing the most common variant.

From a multitude of ablation catheter variants that are adapted to their respective purposes, WO 98/49957 A1, which discloses an ablation device for generating linear lesions between the orifice openings of two pulmonary veins into the atrium of the heart, has been selected as the prior art. According to the disclosure of this reference, a steerable catheter is provided, which carries in front of its distal end an anchoring device in the form of a dilatable balloon to secure the catheter in the ostium of the pulmonary vein.

In this known ablation device the catheter serves not only for the basic positioning of the ablation applicator, but it also carries on its shaft the given ablation electrodes themselves. In this special design the catheter shaft can now be brought proximally relative to the ablation electrodes by means of a second guiding device to the front of the orifice opening of a second pulmonary vein so that the linearly aligned ablation electrodes come to rest on the connecting line between the two orifice openings of two adjacent pulmonary veins. In this manner a linear lesion can reliably be applied between the two orifice openings.

Further embodiments of ablation catheters are shown in, e.g., U.S. Pat. No. 5,239,999 A, WO 95/15115 A1 or WO 95/13111 A1, which disclose ablation electrodes in variably coiled or slightly bent shape.

Recent studies have shown that circular lesions around or at the orifices of the pulmonary veins (hereinafter: pv orifice) into the atrium have been successful, especially for treating the arterial fibrillation of the heart.

The known ablation devices are not practical for lesions of this shape, there being no or hardly any possibility of putting into practice an annular arrangement of the ablation electrodes around or at the pv orifice.

SUMMARY OF THE INVENTION

The invention thus has as its object to present an ablation device whereby a circular lesion around or at a vessel orifice in the heart can be formed in a manner that is reliable and with an application technique that is easy to perform.

According to the invention, a catheter with a linear ablation applicator is provided that is disposed distally or proximally relative to the abutment device of the catheter and can be taken from a straight passive position to a radially expanded, circular-arc-type encircling ablation position and is preferably displaceable axially relative to the abutment device.

The inventive further development of the catheter provides for the ablation applicator, by its encircling in the way of a circular arc in the ablation position, to be brought quasi shape-inherently into a correct position for applying the circular lesion and kept clean by the abutment device. A high degree of application reliably is thus attained in this manner, while accordingly improving the therapeutic success.

The ablation applicator is preferably disposed distally in front of the abutment device so that a lesion can be formed at the pv orifice.

The abutment device is preferably a dilatable balloon on the shaft of the positioning catheter. The diameter of the balloon in its inflated condition must exceed the diameter of the vessel concerned, i.e., it is in an order of magnitude of approximately 15 mm and more. By the aid of the catheter, the balloon is forced against the vessel wall area around the pv orifice, forming an abutment for the ablation applicator that lies distally in front of it. As a result, the ablation applicator can be held properly in the "spandrel-type" area between the balloon front and the pv orifice.

To aid in the creation of the circular-arc-type encircling ablation position, the ablation applicator is formed preferably by a multiple-electrode arrangement, the individual electrodes of which, which are aligned in the axial direction, are composed of a highly flexible material—for example of one spiral winding per electrode, or of a flexible, conducting plastic.

A coverage of at least 180° by the ablation applicator ensures that a completely closed circular lesion can be attained with only one rotation of the ablation catheter.

Even though this is not a direct object of the invention, it needs to be pointed out that the catheter may be provided with known measures for controlling its correct position. The position may, for example, be controlled sonographically by means of an ultrasonic transducer disposed at the tip of the catheter, or by means of a bipolar electrogram, which can be derived by means of a bipolar electrode arrangement at the tip of the catheter. The catheter may also incorporate additional lumen for injecting an X-ray contrast medium, which is injected via the lumen into the pulmonary vein for angiographic imaging.

Further characteristics, details and advantages of the invention will become apparent from the following description, in which embodiments of the object of the invention will be explained in greater detail based on the drawings.

BRIEF DESCRIPTION OF THE PREFERRED EMBODIMENTS

Figure 1:
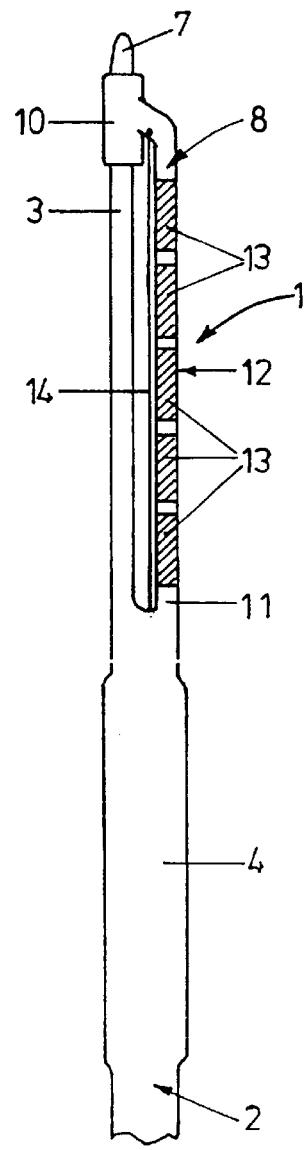
FIG. 1 shows a schematic partial view of an ablation device in its passive position in a first embodiment.

As becomes clear from FIG. 1, the ablation device, which has been marked in its entirety with the numeral 1, incorporates a steerable catheter 2, which has in front of its distal end 3 a dilatable balloon 4. In FIG. 1 the balloon 4 is shown in its non-expanded starting condition, in FIG. 2 it is shown in its expanded condition in which it is positioned in front of an orifice opening 5 of a pulmonary vein 6, shown in a dashed line in FIG. 2, into the atrium of the heart. The catheter 2 may incorporate conventional supplemental devices and may be provided, for example, with a lumen for a guide wire, a deflection device, for the targeted guiding of the distal end 3, etc. Other supplemental devices have furthermore already been mentioned in the introductory part of the specification.

Distally in front of the balloon 4 the catheter 2 is axially divided into the distal steering end 7 and an ablation tip marked in its entirety with 8. The free end of the ablation tip 8 is guided axially movable along the steering end 7 of the catheter 2 by means of a guiding sheath 10.

In the region between the guiding sheath 10 and the transition 11 to the actual catheter 2, an ablation applicator 12 is provided at the ablation tip 8 in the form of five aligned ring electrodes 13, each of which is composed of highly flexible spiral wire. Through these ring electrodes 13 a high-frequency current can be emitted to tissue coming in contact with the same, to form a lesion.

Figure 2:
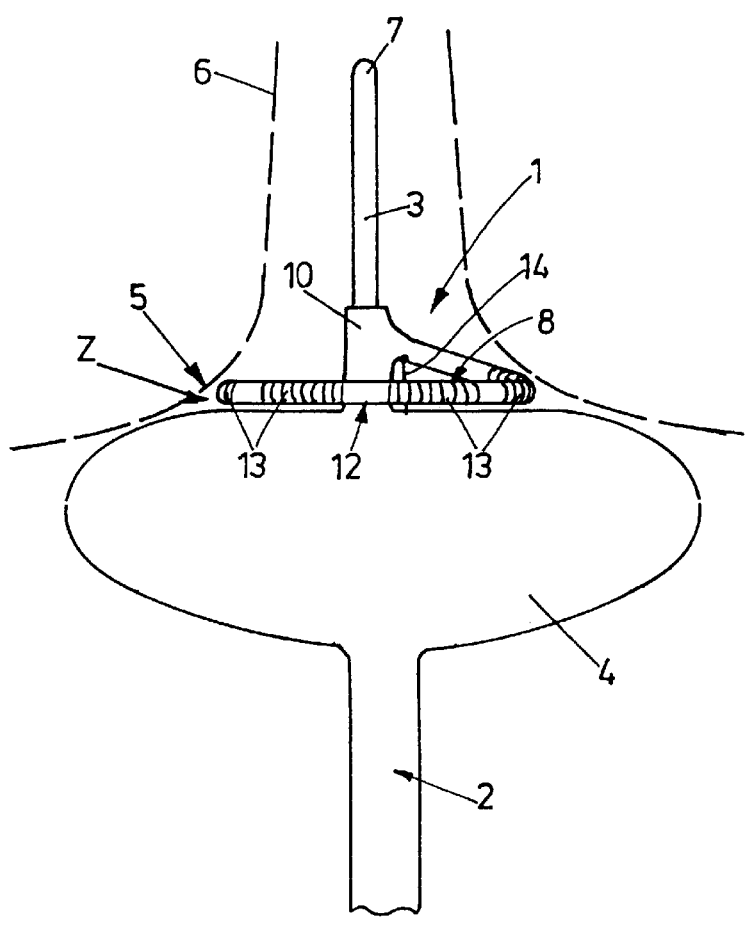
FIG. 2 shows an illustration analogous to FIG. 1 in the ablation position of the device.

FIG. 1 shows the straight position of the ablation applicator 12, from which it can be taken to the radially expanded ablation position shown in FIG. 2 with the aid of a wire pull 14 extending in the catheter 2. For this purpose the wire pull 14 is fixed in the region of the distal guiding sheath 10 and, in the region of the transition 11, extends into the ablation catheter 2. By pulling motions on the wire pull 14 the ablation tip 8 is shifted along the steering end 7 of the positioning catheter 2 in the proximal direction so that the ablation tip 8 expands in the region of the ablation applicator 12 and is brought into a circular-arc-type encircling configuration based on an appropriate pre-shaping of the ablation tip 8. In this case, the positioning catheter 2, with the balloon 4, can be pressed against the myocardial wall around the area of the orifice opening 5. This helps create a sort of abutment that the ablation applicator 12 may be pulled against by the aid of the wire pull 14. It nestles into the annularly encircling spandrel area Z which is formed by the discharging orifice opening 5 and the front of the balloon 4. Thus, the ablation applicator 12 fits tightly on the to be ablated tissue so that tissue denaturation takes place highly efficiently. The ablation applicator 12, in the process, further covers an angle at circumference P of more than 180°so that the ablation applicator 12, in this ablation position, extends over more than half of the circumference of the circular lesion to be formed.

The formation of the circular lesion shall briefly be illustrated below, with the aid of FIGS. 1 and 2. The positioning catheter 2, accordingly, is entered with a non-dilated balloon 4 via a transseptal puncture into the left atrium of the heart where the orifices of all pulmonary veins are mapped with the usual means. After confirming the correct position of the distal end 3 of the positioning catheter 2 inside the orifice opening 5 of the desired pulmonary vein 6, the balloon 4 is dilated and pressed against the myocardial wall around the orifice opening 5.

The ablation tip 8 is subsequently pushed along the steering end 7 of the positioning catheter 2 in the proximal direction until the position in front of the balloon 4 of the positioning catheter 2 is reached that is shown in FIG. 2. The ablation applicator 12 thus lies distally of the balloon 4 in a region relatively deep inside the orifice opening 5. In this position the ring electrodes 13 rest against the vessel wall with the angle at circumference P. By emitting a high-frequency current a portion of the circular lesion is formed. The ablation applicator 12 is then brought at least partially into the passive position shown in FIG. 1, routed by approximately 180° and again expanded in the shape of a circular arc into the ablation position shown in FIG. 2. The ablation applicator 12 thus rests against the pv orifice in the region that has not previously been provided with a lesion. With a renewed emission of a current, the lesion is then completed.

What is claimed is:

1. An ablation device for cardiac tissue, especially for forming a circular lesion in a vessel orifice (5) in the heart, comprising a catheter (2) that is provided in the region of its distal end (3) with an abutment device (4) for holding the distal end (3) of the catheter (2) on a cardiac vessel orifice (5), and a linear ablation applicator (12) that is disposed distally in front of the abutment device (4) of the catheter (2) and can be brought from a straight passive position into a radially expanded, approximately circular-arc-type encircling ablation position, wherein the linear ablation applicator (12) is disposed distally in front of the abutment device (4) of the catheter (2) and is movably guided, at least in its distal end region, by means of a guiding sheath (10) adapted to slide from the distal end section (3) of the catheter (2) toward the abutment device (4) in such a way that through axial movement of the guiding sheath (10) in the proximal direction, the ablation applicator (12) can be brought into the ablation position.

2. An ablation device according to claim 1, wherein the ablation applicator (12) is axially displaceable relative to the abutment device (4).

3. An ablation device according to claim 1, wherein the abutment device is formed by a dilatable balloon (4) on the shaft (7) of the catheter (2).

4. An ablation device according to claim 1, wherein directing the ablation applicator (12) from the passive into the ablation position can be performed by means of wire pull kinematics (14).

5. An ablation device according to claim 1, wherein the ablation applicator (12) is formed by a multiple-electrode arrangement, the individual electrodes (13) of which, which are aligned in the axial direction, are composed of a highly flexible material.

6. An ablation device according to claim 1, wherein the ablation applicator (12) in its circular-arc-type encircling ablation position covers an angle at circumference (P) of at least 180°.

* * * * *